(12) United States Patent
Noda et al.

(10) Patent No.: US 7,842,505 B2
(45) Date of Patent: Nov. 30, 2010

(54) FLUORESCENT LABELING REAGENT

(75) Inventors: Kunihiro Noda, Kanagawa (JP); Ryo Asakura, Kanagawa (JP); Daisuke Saito, Kanagawa (JP); Tetsuhiko Isobe, Kanagawa (JP); Tomohiro Takagi, Kanagawa (JP); Hideki Aizawa, Kanagawa (JP); Michio Ohkubo, Kanagawa (JP)

(73) Assignee: Keio University, Tokyo (JP)

( * ) Notice: Subject to any disclaimer, the term of this patent is extended or adjusted under 35 U.S.C. 154(b) by 883 days.

(21) Appl. No.: 11/678,885

(22) Filed: Feb. 26, 2007

(65) Prior Publication Data

US 2008/0124806 A1 May 29, 2008

(30) Foreign Application Priority Data

Feb. 27, 2006 (JP) .............................. 2006-050944

(51) Int. Cl.
| | |
|---|---|
| G01N 37/00 | (2006.01) |
| G01N 33/533 | (2006.01) |
| G01N 33/543 | (2006.01) |
| G01N 33/551 | (2006.01) |
| C01F 17/00 | (2006.01) |
| G01N 33/553 | (2006.01) |

(52) U.S. Cl. .......................... 436/56; 436/523; 436/524; 436/525; 436/546; 423/263; 536/25.32

(58) Field of Classification Search .................... 436/56
See application file for complete search history.

(56) References Cited

U.S. PATENT DOCUMENTS

| 5,990,479 A | 11/1999 | Weiss et al. |
| 6,277,841 B1 | 8/2001 | Rajagopalan et al. |
| 2004/0061433 A1* | 4/2004 | Izuno et al. ................. 313/498 |
| 2005/0014283 A1* | 1/2005 | Matsuura et al. ............ 436/166 |
| 2007/0087195 A1* | 4/2007 | Meyer et al. ................. 428/403 |
| 2008/0017802 A1* | 1/2008 | Nakamura et al. ...... 250/361 R |

FOREIGN PATENT DOCUMENTS

| JP | 2003-525282 | 8/2003 |
| JP | 2006162284 A * | 6/2006 |

* cited by examiner

Primary Examiner—Jill Warden
Assistant Examiner—Jennifer Wecker
(74) Attorney, Agent, or Firm—Oblon, Spivak, McClelland, Maier & Neustadt, L.L.P.

(57) ABSTRACT

A fluorescent labeling reagent of the present invention includes an inorganic fluorescent particle and a material (A) having a material (B) of biological origin adsorbed or bound thereto. The inorganic fluorescent particle is integrated with the material (A) so as to form the reagent of the present invention. The inorganic fluorescent particle used in the present invention is capable of emitting light with a wavelength of 650 nm to 1600 nm in the infrared region or the near-infrared region which can be detected by means of Si—CCD or InGaAs—PD and can penetrate an $H_2O$ rich sample when excited by light with a wavelength of 650 nm or longer which has the shortest transparent wavelength of AlIn-GaP-LD including oxygen adsorption type hemoglobin used for DVDs etc.

8 Claims, 3 Drawing Sheets

FLUORESCENT LABELING REAGENT

BACKGROUND OF THE INVENTION

1. Technical Field

The present invention relates to a fluorescent labeling reagent for a biological label to detect a biological material in medical and biological fields or the like.

2. Related Arts

In recent years, developments have been made on various measurement methods and materials for optically detecting a biomolecule, using a fluorescent labeling compound in which a material capable of being adsorbed on or bound to a specific biomolecule contains a fluorescent material. The measurement using such a fluorescent labeling compound includes, for example, DNA chip for detecting a specific DNA sequence and a detection of antigenic material using antibody. The measurement using the fluorescent labeling compound is also applicable to Flow Cytometry which detects the specific material or biological cell having the specific material. Further, the fluorescent labeling compounds are used in Bio-imaging to visualize by fluorescence where the specific materials exist in biological body, by directly dispersing the fluorescent labeling compounds into the biological body.

These use the phenomenon that, when the fluorescent labeling compound which has been adsorbed on or bound to the biomolecule is exposed to light, the fluorescent material absorbs the light so as to emit light at a specific wavelength. For the fluorescent material contained in the fluorescent labeling compounds, the organic dye, metal complex, semiconductor nanoparticle, and the like are generally used.

For example, U.S. Pat. No. 5,990,479 discloses Group II-VI semiconductor nanocrystals for biological probes as visible luminescent inorganic particles. These emit light in visible region by using short-wavelength UV light or visible light such as blue light, and the like as an excitation light source.

Further, JP 2003-525282 (a published Japanese translation of PCT application) discloses fluorescent quinoline ligands as a fluorescent material emitting in the near-infrared region (NIR). This publication describes fluorescent organometallic complexes.

Fluorescent probes emitting in visible region have been mainly used as fluorescent probes to examine the biomedical tissues. This reason is the conveniences such that it is possible to directly confirm the luminescence state with the naked eyes and that the images can be recorded with various existing imaging devices. However, it is required to use the excitation light source which has a wavelength shorter than the fluorescence wavelength of the fluorescent material, and therefore, there is a problem that the excitation light source having such a shorter wavelength, especially a laser source, is expensive.

Further, in the case of using a xenon lamp or LED, since its spectrum is broad, a component of the fluorescence wavelength regions of the spectrum must be cut by using a proper diffraction grating or light filter, thereby causing the complication of the measurement system and the decrease in excitation light intensity.

Furthermore, in the case of using ultraviolet ray as excitation light, higher intensity of the light may cause destruction of the biomedical tissues such as cells. In addition, since many of the biomedical tissues derived from higher organisms such as mammal contain a dye which easily absorbs the visible light, there is also the problem that the excited light cannot penetrate into the specimen or that the radiated fluorescent cannot be taken out from the specimen.

On the other hand, there is a fluorescent material for biological label containing an organic molecule or an organometallic complex which absorbs the near-infrared light and then radiates the near-infrared light. However, the fluorescent material containing the organic molecule is gradually destroyed due to the repetition of the interaction with light, thereby causing the problem of the color fading that the fluorescence intensity decreases gradually while measuring it for a long time.

Further, the fluorescent labeling compound using the organic dye has problems of an unstable fluorescence wavelength and a short life. The fluorescent labeling compound using the organometallic complex has a problem that the fluorescence wavelength and intensity are liable to variation due to the ligands and the like. As a material capable of solving the problems of the instabilities, use of semiconductor nanoparticle for the fluorescent material has been examined. However, control of the particle size of the nanoparticle is not easy, resulting in occurrence a problem that the fluorescence wavelength varies depending on the particle size of the semiconductor nanoparticle, and therefore, the detected fluorescent intensity varies. In addition, in order to control nonradiative trap level formed on the surface of the semiconductor nanoparticle and cause the semiconductor nanoparticle to emit light efficiently, a particle having a structure called a core shell structure in which the semiconductor nanoparticle is coated with other semiconductors etc. has been generally manufactured. However, this increases the manufacturing cost. Moreover, there is a problem that the semiconductor nanopaticle made of cadmium or selenium has toxicity.

BRIEF SUMMARY OF THE INVENTION

The present invention has an object to provide a stable and low-cost fluorescent labeling reagent for biological label to detect a biological material.

A fluorescent labeling reagent for biological label according to a first aspect of the present invention comprises: an inorganic fluorescent particle capable of emitting light with a wavelength of 650 nm to 1600 nm when excited by light with a wavelength of 650 nm or longer; and a material (A) having a material (B) of biological origin adsorbed or bound thereto, the material (A) being integrated with the inorganic fluorescent particle.

A fluorescent labeling reagent for biological label according to a second aspect of the present invention is a fluorescent labeling reagent in which the inorganic fluorescent particle has a primary particle size of 1 nm to 5000 nm A fluorescent labeling reagent for biological label according to a third aspect of the present invention is a fluorescent labeling reagent in which the inorganic fluorescent particle comprises a rare earth element as a dopant having a fluorescent spectrum in near-infrared region.

A fluorescent labeling reagent for biological label according to a fourth aspect of the present invention is a fluorescent labeling reagent in which the inorganic fluorescent particle comprises one or more rare earth element as dopants selected from the group consisting of cerium, praseodymium, neodymium, gadolinium, holmium, erbium, thulium, ytterbium, europium, terbium, samarium, and dysprosium.

A fluorescent labeling reagent for biological label according to a fifth aspect of the present invention is a fluorescent labeling reagent in which the inorganic fluorescent particle has a garnet structure of yttrium, aluminum and oxygen and is a crystalline particle in which at least one of rare earth elements capable of producing fluorescence is incorporated into the garnet structure.

A fluorescent labeling reagent for biological label according to a sixth aspect of the present invention is a fluorescent labeling reagent in which the integration of the inorganic fluorescent material and the material (A) is carried out by means of chemical reaction in which a modification group introduced onto a surface of the inorganic fluorescent particle is directly bound to an organic molecule of the material (B).

A fluorescent labeling reagent for biological label according to a seventh aspect of the present invention is a fluorescent labeling reagent in which the material (A) is a functional bead of an inorganic material or polymer material of which surface is chemically modified to have a molecule capable of adsorbing or binding to a specific biomolecule, and the integration of the inorganic fluorescent material and the material (A) is carried out by dispersing the inorganic fluorescent particle into the functional bead.

A fluorescent labeling reagent for biological label according to a eighth aspect of the present invention is a fluorescent labeling reagent in which the direct binding of the inorganic fluorescent particle and the material (B) is carried out by the steps of: subjecting the inorganic fluorescent particle to a surface treatment by means of reaction with silane coupling agent having amino group, thiol group, or carboxyl group so that the amino group, thiol group, or carboxyl group is introduced onto a surface of the inorganic fluorescent particle, and binding the amino group, thiol group, or carboxyl group to the material (B) selected from the group consisting of avidin, streptavidin, fusion protein of avidin or streptavidin, biotin, antigen, antibody, DNA, and RNA.

A fluorescent labeling reagent for biological label according to a ninth aspect of the present invention is a fluorescent labeling reagent in which the introduction of amino group is carried out by using aminoalkyl thiol compound and utilizing a binding of the inorganic fluorescent particle and thiol.

A fluorescent labeling reagent for biological label according to a tenth aspect of the present invention is a fluorescent labeling reagent in which the functional bead has a diameter of 0.1 μm to 100 μm and is selected from the group consisting of polymer beads including polystyrene bead, polypropylene bead, cross-linked acrylic bead, and polylactide bead, magnetic beads, glass beads, metallic beads, and the surface of the functional bead is chemically modified to specifically adsorb or bind to the material of biological origin.

BRIEF DESCRIPTION OF THE DRAWINGS

The above and other objects and features of the invention will appear more fully hereinafter from a consideration of the following description taken into connection with the accompanying drawing wherein one example is illustrated by way of example, in which.

DETAILED DESCRIPTION OF THE INVENTION

Figure 1:
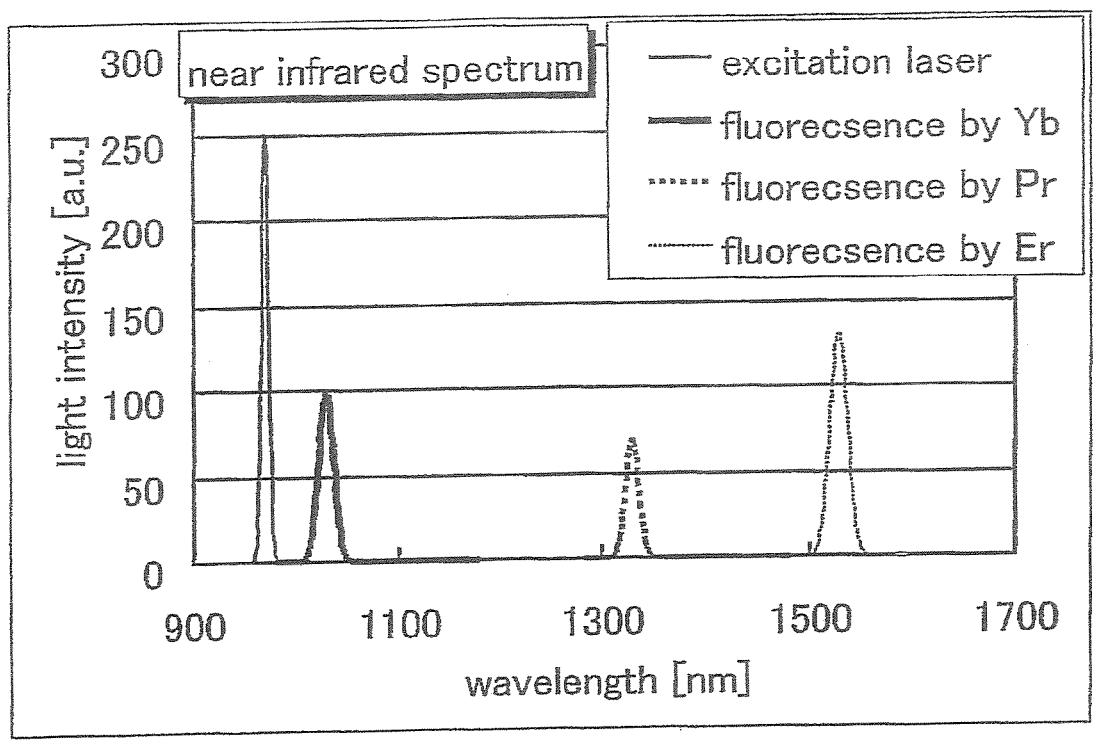
FIG. 1 is a graph showing spectra of the excitation laser light and the fluorescence from the reagents detected when performing multicoloring in Example 2 of the present invention.

Embodiments of the present invention will be described below.

A fluorescent labeling reagent of the present invention includes an inorganic fluorescent particle and a material (A) having a material (B) of biological origin adsorbed or bound thereto. The inorganic fluorescent particle is integrated with the material (A) so as to form the reagent of the present invention. The inorganic fluorescent particle used in the present invention is capable of emitting light with a wavelength of 650 nm to 1600 nm in the infrared region or the near-infrared region which can be detected by means of Si—CCD or InGaAs—PD and can penetrate an $H_2O$ rich sample when excited by light with a wavelength of 650 nm or longer which has the shortest transparent wavelength of AlInGaP-LD including oxygen adsorption type hemoglobin used for DVDs etc.

The inorganic fluorescent particle of the present invention is an aggregate of atoms or molecules and excited by light stimulation so as to emit light with a different wavelength from the excitation light. The inorganic fluorescent particle includes, for example, a particle in which a crystalline or noncrystalline matrix incorporates atoms and molecules having the fluorescent or luminescent property by light excitation, and a direct transition type semiconductor.

Specifically, the inorganic fluorescent particle includes one or more rare earth element as dopants selected from the group consisting of cerium, praseodymium, neodymium, gadolinium, holmium, erbium, thulium, ytterbium, europium, terbium, samarium, and dysprosium, which are capable of producing fluorescence.

The inorganic fluorescent particle includes a rare earth element as a dopant having a fluorescent spectrum in near-infrared region. The rare earth element having a fluorescent spectrum in near-infrared region includes praseodymium, neodymium, dysprosium, holmium, erbium, thulium, and ytterbium. The inorganic fluorescent particle includes, as dopants, one or more rare earth elements described above.

Concrete example of the inorganic fluorescent particle is a crystalline particle in which at least one of the rare earth elements described above is incorporated into the matrix having a garnet structure of yttrium, aluminum and oxygen (hereinafter YAG).

The above-described inorganic fluorescent particle has a primary particle size of 1 nm to 5000 nm. This is because the particle having a primary particle size of 1 nm or less results in comparable size to the complex material of molecules of biological origin and the particle having a primary particle size of 5000 nm or more results in comparable size to a cell itself.

The above-described inorganic fluorescent particle which is capable of emitting light with a wavelength of 650 nm to 1600 nm when excited by light with a wavelength of 650 nm or longer is integrated with the material (A) having the material (B) of biological origin adsorbed or bound thereto, thereby obtaining the fluorescent labeling reagent as a fluorescent labeling compound capable of labeling a specific biomolecule.

Alternatively, the fluorescent labeling reagent may be the inorganic fluorescent particle integrated with the material (B) of biological origin adsorbed or bound thereto. Examples of method of the integration of the inorganic florescent particle and the material (B) include, but are not limited to, the following methods:

(i) a modification group introduced onto the surface of the inorganic fluorescent particle is directly bound to an organic molecule of the material (B) by chemical reaction.

(ii) a functional bead of an inorganic material or polymer material of which surface is chemically modified to have a molecule capable of adsorbing or binding to a specific biomolecule is used as the material (A) and the inorganic fluorescent particles are dispersed into the functional bead.

The method of the direct binding of the inorganic fluorescent particle and an organic compound of the material (B) is that, for example, the inorganic fluorescent particle is subjected to a surface treatment by means of reaction with silane coupling agent having amino group such as APS (aminopropyl silane) so that the amino group is introduced onto the surface of the inorganic fluorescent particle and the amino group is bound to the material (B) such as avidin, streptavidin, fusion protein of avidin or streptavidin, biotin, antigen, antibody, DNA, and RNA. A method of the introduction of the amino group is, for example, using aminoalkyl thiol compound such as aminoethanethiol and utilizing of a binding of the inorganic fluorescent particle and thiol.

The inorganic fluorescent particle having amino group attached to the surface thereof can be coupled to avidin, streptavidin, fusion protein of avidin or streptavidin, biotin, antigen, antibody, DNA, and RNA by using bifunctional cross-linking agent such as EMCS (N-(6-maleimidocaproyloxy)succinimide or by forming amide binding with carboxyl group activated by NHS ester (N-hydroxysuccinimidyl ester) and the like. The avidin, streptavidin, fusion protein of avidin or streptavidin, biotin, antigen, antibody, DNA, and RNA bound to the inorganic fluorescent particle can be used as a detection antibody and an enzyme for detection.

In addition, the method of the direct binding of the inorganic fluorescent particle and an organic compound of the material (B) may be that the inorganic fluorescent particle is subjected to a surface treatment by means of reaction with silane coupling agent having thiol group or carboxyl group so that the thiol group or carboxyl group is introduced onto the surface of the inorganic fluorescent particle and the thiol group or carboxyl group is bound to the material (B) such as avidin, streptavidin, fusion protein of avidin or streptavidin, biotin, antigen, antibody, DNA, and RNA.

In the case where the inorganic fluorescent particles are incorporated in the functional bead, it can be used for detection and concentration measurement of biomolecule by using flow cytometry technique. The functional bead in this case has a diameter of 0.1 μm to 100 μm and includes polymer beads such as polystyrene bead, polypropylene bead, crosslinked acrylic bead, and polylactide bead, magnetic beads, glass beads, metallic beads, and the surface of the functional bead is chemically modified to specifically adsorb or bind to the material of biological origin. Method of dispersing the inorganic fluorescent particles into the functional bead is not particularly limited. For example, in the case of using polymer bead as the functional bead, the inorganic fluorescent particles are dispersed in a solvent and then the bead is placed in the solvent to be swollen, whereby the inorganic fluorescent particles can be incorporated in the functional bead.

Examples of the present invention will be described in detail below.

EXAMPLE 1

Acetic acid compound complex doped with rare earth elements was added to yttrium acetate and aluminum isopropoxide and they were mixed into 1,4-butanediol solvent. Then, the mixture was subjected to the glycothermal treatment using the autoclave, thereby obtaining a YAG (Yttrium Aluminum Garnet) crystalline particle including a fluorescent rare earth dopant.

EXAMPLE 2

Three types of fluorescent reagents including Yb, Pr, and Er as a dopant, respectively, were simultaneously excited by an LD which radiates a laser light having the wavelength of 0.97 nm. Then, fluorescence from the respective reagents were divided into different groups of wavelengths by using a filter. The fluorescence wavelengths of the fluorescent reagents of Yb, Pr, and Er were 1.03 nm, 1.33 nm, and 1.53 nm, respectively. InGaAs or Ge photodiode or photoelectron multiplier was used as an optical detector. FIG. 1 is a graph showing spectra of the excitation laser light and the fluorescence from the respective reagents detected when performing multicoloring.

EXAMPLE 3

Two types of fluorescent reagents including Nd and Er as a dopant, respectively, were simultaneously excited by an LD which radiates a laser light having the wavelength 0.80 nm. Then, fluorescence from the respective reagents were divided into different groups of wavelengths by using a filter. The fluorescence wavelengths of the fluorescence reagents of Nd and Er were 1.06 nm and 1.53 nm, respectively. InGaAs or Ge photodiode or photoelectron multiplier was used as an optical detector.

EXAMPLE 4

Figure 2:
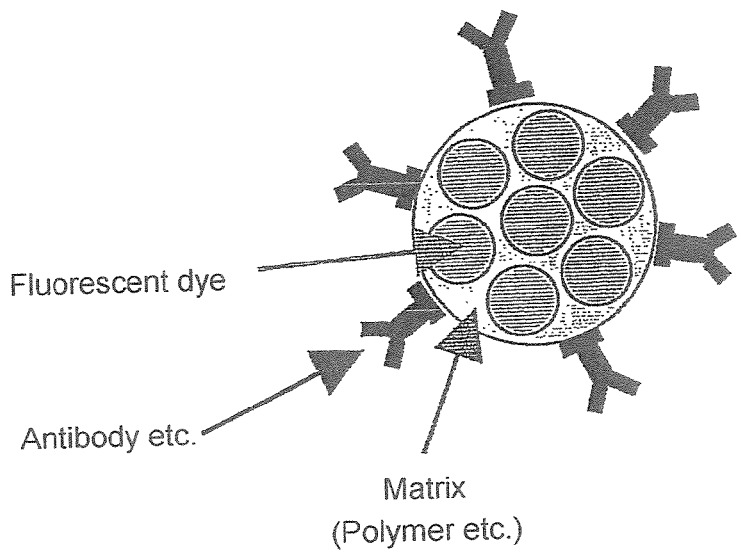
FIG. 2 is a schematic view showing a composite fluorescent particle in which the surface of the matrix bead including the fluorescent particles was modified to have antibodies having the target substance selectivity in Example 4 of the present invention.

YAG crystalline particles with a diameter of several tens nm (nanometers) including approximately 1% rare earth elements were incorporated in a particle with a diameter of approximately 1 μm including a matrix which has a low interactive property to light such as silica glass and PMMA. Then, the surface thereof was modified to have antibody molecules depending upon target substances. FIG. 2 is a schematic view showing a composite fluorescent particle in which the surface of the matrix bead including the fluorescent particles was modified to have antibodies having the target substance selectivity.

EXAMPLE 5

The above-described composite fluorescent particle for labeling a biological material was mixed into a liquid sample which may include a biological material to be labeled.

EXAMPLE 6

The composite fluorescent particle for a label to detect a material such as DNA having a specific base sequence and protein was mixed into a liquid sample which may include the material. Then, the detection of the material was performed by using a DNA chip and a detection device.

EXAMPLE 7

Figure 3:
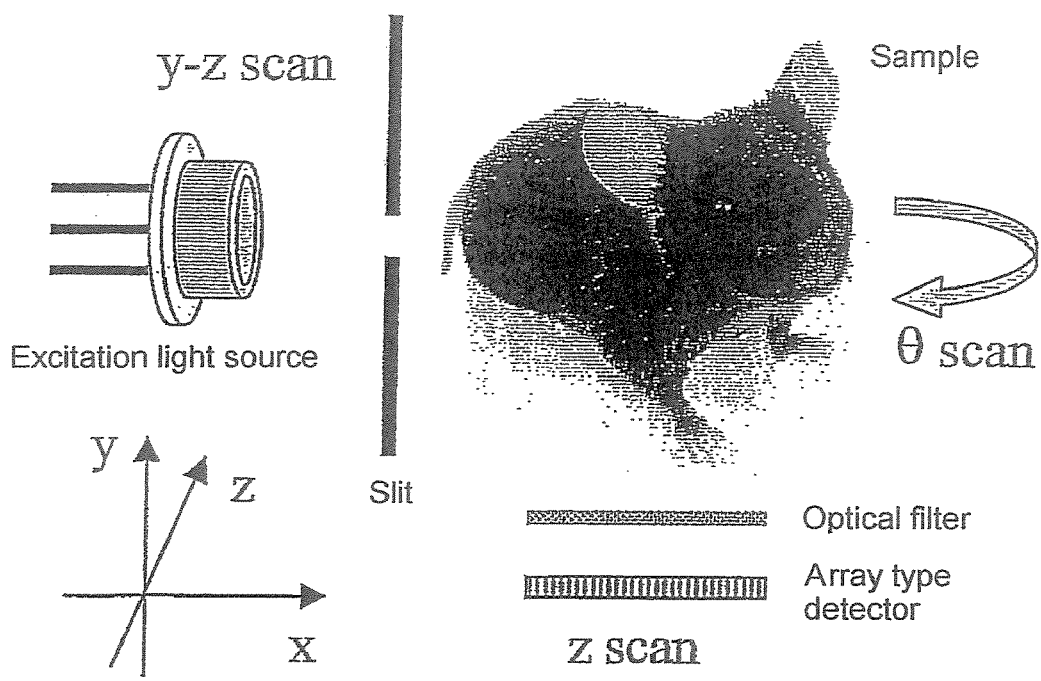
FIG. 3 is a schematic view showing an optical system for carrying out the three-dimensional imaging by using a collimated laser beam scan in Example 7 of the present invention.

In order to obtain the three-dimensional image of biological samples, e.g. the three-dimensional distribution image of blood vessels in organ, labeling reagents each including a fluorescent particle were given to the sample, then the location and/or the angle of each reagent were scanned while irradiating the sample with the collimated laser beam for excitation from the direction perpendicular to the imaging direction. A three-dimensional image was obtained from the fluorescent image thus detected. FIG. 3 is a schematic view showing an optical system for carrying out the three-dimensional imaging by using a collimated laser beam scan.

EXAMPLE 8

Figure 4:
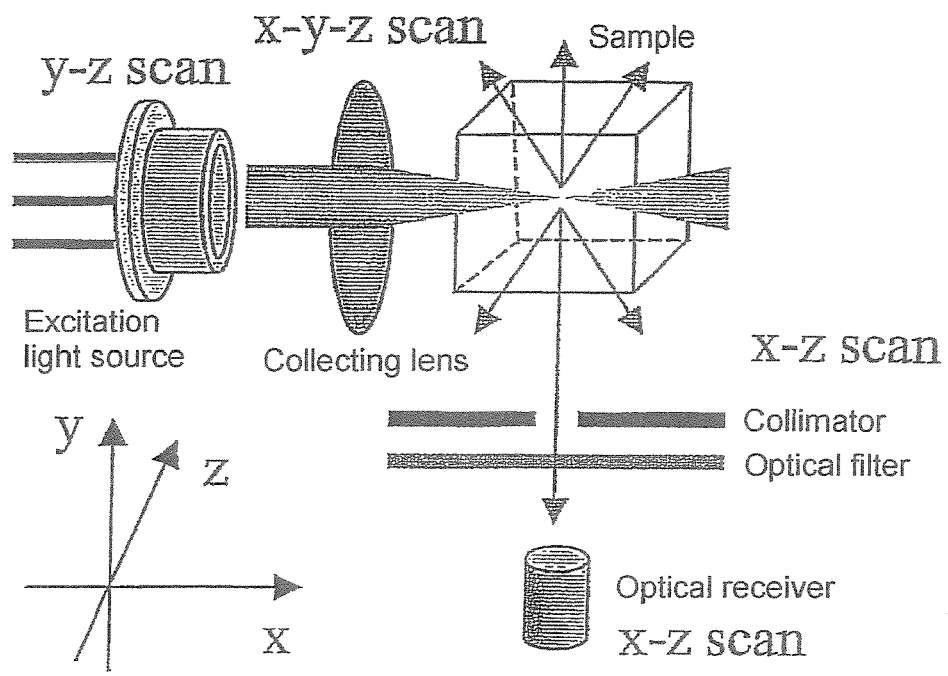
FIG. 4 is a schematic view showing an optical system for carrying out the three-dimensional imaging by the laser-spot scan in Example 8 of the present invention.
Figure 5:
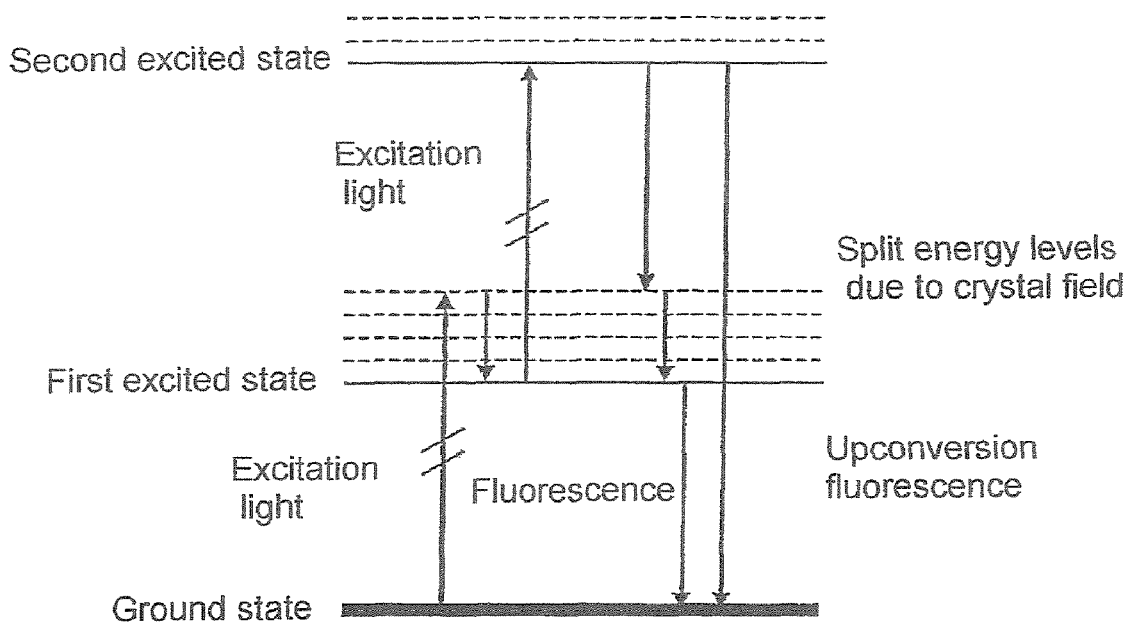
FIG. 5 shows the energy transition state with respect to the upconversion fluorescence of a type realized by a higher energy level of a fluorescent ion such as rare earth in Example 8 of the present invention.

In order to obtain the three-dimensional image of biological samples, e.g. the three-dimensional distribution image of blood vessels in organ, labeling reagents each including a fluorescent particle which includes rare earth element such as Tm having the infrared fluorescence were given to the sample, then an excitation laser-spot was moved three-dimensionally so as to cause the labeling reagents to radiate upconversion fluorescence at the spots, followed by detecting the upconversion fluorescent only by using a filter. A three-dimensional image was obtained from the result of the three-dimensional scan. FIG. 4 is a schematic view showing an optical system for carrying out the three-dimensional imaging by the laser-spot scan. FIG. 5 shows the energy transition state with respect to the upconversion fluorescence of a type realized by a higher energy level of a fluorescent ion such as rare earth According to the present invention, the inorganic fluorescent particle capable of absorbing the near-infrared light is used as a fluorescent labeling reagent, thus the common light source of the near-infrared radiation used in optical communications and the like can be used as an excitation light source for measurement and a detection device. This light source of the near-infrared radiation has advantages in a high power and a long operating life and is obtainable cheaply and easily. Therefore, using the fluorescent labeling reagent of the present invention makes it possible to reduce the total cost.

Further, according to the present invention, the light of the near-infrared radiation shows a high permeability to a biological tissue including dyes capable of absorbing the visible light such as hemoglobin and melanin, making it possible to easily obtain the information within the measuring samples and obtain the three-dimensional images as well.

Still further, according to the present invention, the inorganic fluorescent particle shows a high stability to the interaction with light, thereby preventing the decrease in the fluorescent intensity even when exposed to intense excitation light for a long time. Therefore, it is possible to irradiate the measuring samples with a high intense excitation light. This enables a highly precise measurement even when (i) a small amount of the fluorescent reagent is used, (ii) a measuring sample is thick, and (iii) a fluorescent intensity becomes weak.

As described above, the fluorescent labeling reagent of the present invention can be used for biomolecule detection reagent.

The present invention is not limited to the above described embodiments and various and modifications may be possible without departing from the scope of the present invention.

This application is based on the Japanese Patent application No. 2006-050944 filed on Feb. 27, 2006, entire content of which is expressly incorporated by reference herein.

What is claimed is:

1. A fluorescent labeling reagent comprising:
   an inorganic fluorescent particle capable of emitting light with a wavelength of 650 nm to 1600 nm when excited by light with a wavelength of 650 nm or longer; and
   a material (A) capable of absorbing or binding to a material (B) of biological origin, the material (A) being integrated with the inorganic fluorescent particle,
   wherein the material (A) is a functional bead matrix composed of an inorganic material or a polymer material of which surface is chemically modified to have a molecule capable of absorbing or binding to a specific biomolecule,
   wherein the inorganic fluorescent particle is dispersed into the functional bead matrix, whereby the material (A) is integrated with the inorganic fluorescent particle,
   wherein the inorganic fluorescent particle comprises one or more rare earth element capable of producing fluorescence as dopants selected from the group consisting of cerium, praseodymium, neodymium, gadolinium, holmium, erbium, thulium, ytterbium, europium, terbium, samarium, and dysprosium, and
   wherein the inorganic fluorescent particle has a garnet structure of yttrium, aluminum and oxygen, and the inorganic fluorescent particle is a crystalline particle in which the one or more rare earth element is incorporated into the garnet structure.

2. The fluorescent labeling reagent according to claim 1, wherein the inorganic fluorescent particle has a primary particle size of 1 nm to 5000 nm.

3. The fluorescent labeling reagent according to claim 1, wherein the rare earth element has a fluorescent spectrum in the near-infrared region.

4. The fluorescent labeling reagent according to claim 1,
   wherein the functional bead matrix has a diameter of 0.1 μm to 100 μm,
   wherein the functional bead matrix is selected from the group consisting of a polystyrene bead matrix, a polypropylene bead matrix, a cross-linked acrylic bead matrix, a polylactide bead matrix, a magnetic bead matrix, a glass bead matrix, and a metallic bead matrix, and
   wherein the surface of the functional bead is chemically modified to have the capability of specifically absorbing or binding to the material of biological origin.

5. The fluorescent labeling reagent according to claim 1, wherein the material (A) is integrated with the inorganic fluorescent particle by a chemical reaction, via a modification group introduced onto a surface of the inorganic fluorescent particle, such that the inorganic fluorescent particle has the capability of being directly bound to the material of the biological origin.

6. The fluorescent labeling reagent according to claim 1, wherein the material (A) is integrated with the inorganic fluorescent particle by a silane coupling agent having an amino group, a thiol group, or a carboxyl group so that the amino group, the thiol group, or the carboxyl group is introduced onto a surface of the inorganic fluorescent particle.

7. The fluorescent labeling reagent according to claim 6, wherein the introduction of amino group is carried out by using aminoalkyl thiol compound and utilizing a binding of the inorganic fluorescent particle and thiol.

8. The fluorescent labeling reagent according to claim 1, wherein the material (B) is selected from the group consisting of avidin, streptavidin, fusion protein of avidin or streptavidin, biotin, antigen, antibody, DNA, and RNA.

* * * * *